United States Patent
Morgan, III et al.

(10) Patent No.: US 10,322,198 B2
(45) Date of Patent: Jun. 18, 2019

(54) FRESHENING COMPOSITIONS COMPRISING ISOPROPYL MYRISTATE

(71) Applicant: The Procter & Gamble Company, Cincinnati, OH (US)

(72) Inventors: George Kavin Morgan, III, Hamilton, OH (US); Stephen Jeffrey Blessing, Fairfield, OH (US); Ronald David Turner, Walton, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 322 days.

(21) Appl. No.: 15/205,314

(22) Filed: Jul. 8, 2016

(65) Prior Publication Data
US 2018/0008740 A1 Jan. 11, 2018

(51) Int. Cl.
*A61L 9/01* (2006.01)
*A61L 9/03* (2006.01)
*A61L 9/14* (2006.01)

(52) U.S. Cl.
CPC .............. *A61L 9/01* (2013.01); *A61L 9/032* (2013.01); *A61L 9/037* (2013.01); *A61L 9/14* (2013.01); *A61L 2209/131* (2013.01); *A61L 2209/132* (2013.01); *A61L 2209/135* (2013.01)

(58) Field of Classification Search
CPC ............. A61L 9/01; A61L 9/032; A61L 9/037
See application file for complete search history.

(56) References Cited

U.S. PATENT DOCUMENTS

| 5,362,715 A | 11/1994 | Cohen et al. |
| 6,172,037 B1 | 1/2001 | Perring et al. |
| 2002/0193281 A1 | 12/2002 | Mansfeld et al. |
| 2003/0068295 A1 | 4/2003 | Rohde et al. |
| 2004/0082488 A1 | 4/2004 | Duprey et al. |
| 2004/0190883 A1* | 9/2004 | Kompara ............ A61L 9/035 392/390 |
| 2004/0266638 A1 | 12/2004 | Requejo et al. |
| 2006/0002863 A1 | 1/2006 | Schmelzer et al. |
| 2008/0248120 A1 | 10/2008 | Anderson et al. |
| 2009/0238787 A1 | 9/2009 | Finke et al. |
| 2010/0001091 A1 | 1/2010 | Bara et al. |

(Continued)

FOREIGN PATENT DOCUMENTS

| CN | 101633868 B | 8/2012 |
| CN | 104186571 A | 12/2014 |

(Continued)

OTHER PUBLICATIONS

PCT Search Report dated Jun. 27, 2017; PCT/US2017/039456; 15 Pages.

*Primary Examiner* — Kevin Joyner
(74) *Attorney, Agent, or Firm* — Abbey A. Lopez

(57) ABSTRACT

A liquid freshening composition is provided. The liquid freshening product includes about 0.5 wt. % to about 15 wt. % isopropyl myristate, by weight of the liquid freshening composition and greater than 40 wt. % of one or more perfume raw materials. The liquid freshening composition has a vapor pressure at 25° C. of about 0.03 Torr to about 1.0 Torr. The liquid freshening composition may be used with air freshening products having a delivery engine such as a wick, breathable membrane, gel, porous and semi-porous substrate, and combinations thereof.

18 Claims, 9 Drawing Sheets

(56) References Cited

U.S. PATENT DOCUMENTS

| | | |
|---|---|---|
| 2010/0056422 A1 | 3/2010 | Lammert et al. |
| 2010/0308126 A1 | 12/2010 | Gruenbacher et al. |
| 2011/0182832 A1 | 7/2011 | Bradshaw et al. |
| 2013/0058886 A1* | 3/2013 | Diersing .................. A61K 8/31 424/76.1 |
| 2014/0235520 A1 | 8/2014 | Bradshaw et al. |
| 2018/0078666 A1* | 3/2018 | Blondeau .................. A61L 9/01 |

FOREIGN PATENT DOCUMENTS

| | | |
|---|---|---|
| CN | 104186574 A | 12/2014 |
| CN | 104186575 A | 12/2014 |
| CN | 104186577 A | 12/2014 |
| CN | 104186579 A | 12/2014 |
| CN | 104606697 A | 5/2015 |
| CN | 104922001 A | 9/2015 |
| EP | 1 050 311 A1 | 11/2000 |
| EP | 1 759 716 A1 | 3/2007 |
| WO | WO96/08425 A2 | 3/1996 |
| WO | WO 2006/010282 A1 | 2/2006 |
| WO | WO 2007/052016 A2 | 5/2007 |

* cited by examiner

FRESHENING COMPOSITIONS COMPRISING ISOPROPYL MYRISTATE

FIELD

The present application relates to freshening compositions comprising isopropyl myristate that provide long-lasting scent delivery through a porous or microporous substrate.

BACKGROUND

Air care products, such as wick-based or microporous-membrane based products, may be used to deliver various freshening compositions into the air or onto a surface. The freshening compositions used with such air care products may include volatile materials such as perfume. The volatility of the freshening composition varies based on the particular components of the composition. As the vapor pressure of a freshening composition increases, the rate at which the freshening composition volatilizes also increases. As a result, the lifespan of an air care product can be dependent upon the particular freshening composition used. In some cases, carriers such as solvents and diluents are used to slow down the rate of evaporation of a particular freshening composition. In highly volatile freshening compositions, a high level of carriers may be used to slow down the evaporation of the freshening composition. Adding carriers and other materials to slow down the evaporation rate of the freshening composition may significantly reduce the level perfume materials in the freshening composition or may change the character of the freshening composition and scent intensity.

Thus, it would be beneficial to provide a freshening composition that delivers long-lasting scent irrespective of the vapor pressure of the composition without significantly altering the formulation or character of the freshening composition.

SUMMARY

"Combinations:"

A. A liquid freshening composition comprising:
about 0.5 wt. % to about 15 wt. % isopropyl myristate, by weight of the liquid freshening composition; and
greater than 30 wt. % of one or more non-functional perfume raw materials, by weight of the liquid freshening composition,
wherein the liquid freshening composition has a vapor pressure at 25° C. of about 0.03 Torr to about 1.0 Torr.

B. The liquid freshening composition of Paragraph A further comprising less than 50 wt. % of a carrier, more preferably less than 30 wt. % of a carrier, by weight of the liquid freshening composition.

C. The liquid freshening composition of Paragraph A or B comprising about 0.5 wt. % to about 15 wt. %, preferably about 0.50 wt. % to about 10.0 wt. %, more preferably about 0.75 wt. % to about 3.0 wt. %, most preferably about 1.0 wt. % to about 2.0 wt. % isopropyl myristate, by weight of the liquid freshening composition.

D. The liquid freshening composition of any of Paragraphs A through C, wherein the liquid freshening composition has a vapor pressure at 25° C. of about 0.03 Torr to about 0.75 Torr.

E. An air freshener product comprising:
a liquid freshening composition comprising about 0.5 wt. % to about 15 wt. % isopropyl myristate and greater than 40 wt. % of one or more perfume raw materials, by weight of the liquid freshening composition, wherein the liquid freshening composition has a vapor pressure at 25° C. of about 0.03 Torr to about 1.0 Torr;
a reservoir for containing the liquid freshening composition; and
a delivery engine in fluid communication with the freshening composition, wherein the delivery engine is selected from the group consisting of: wick, breathable membrane, gels, porous and semi-porous substrate, and combinations thereof.

F. The air freshener product of Paragraph E further comprising a heater, wherein the heater is configured to heat the delivery engine to a temperature in the range of about 50° C. to about 150° C.

G. The air freshener product Paragraph E or F, wherein the liquid freshening composition comprises less than 30 wt. % of a carrier, by weight of the liquid freshening composition.

H. The air freshener product of any of Paragraphs E through G, further comprising about 0.5 wt. % to about 15 wt. %, preferably about 0.50 wt. % to about 10.0 wt. %, more preferably about 0.75 wt. % to about 3.0 wt. %, most preferably about 1.0 wt. % to about 2.0 wt. % isopropyl myristate, by weight of the liquid freshening composition.

I. The air freshener product of any of Paragraphs E through H, wherein the liquid freshening composition has a vapor pressure at 25° C. of about 0.03 Torr to about 0.75 Torr.

J. A method of freshening the air comprising the steps of:
providing a freshening composition comprising about 0.5 wt. % to about 15 wt. % isopropyl myristate and greater than 40 wt. % of one or more perfume raw materials, by weight of the liquid freshening composition, wherein the liquid freshening composition has a vapor pressure at 25° C. of about 0.03 Torr to about 1.0 Torr;
delivering the liquid freshening composition to a delivery engine, wherein the delivery engine is selected from the group consisting of: wick, breathable membrane, gels, porous and semi-porous substrate, and combinations thereof; and
dispersing the liquid freshening composition into the air.

K. The method of Paragraph J further comprising the step of heating the delivery engine to a temperature in the range of about 50° C. to about 150° C.

L. The method of Paragraph J or K further comprising less than 50 wt. % of a carrier, more preferably less than 30 wt. % of a carrier, by weight of the liquid freshening composition.

M. The method of any of Paragraphs J through L comprising about 0.5 wt. % to about 15 wt. %, preferably about 0.50 wt. % to about 10.0 wt. %, more preferably about 0.75 wt. % to about 3.0 wt. %, most preferably about 1.0 wt. % to about 2.0 wt. % isopropyl myristate, by weight of the liquid freshening composition.

N. The method of any of Paragraphs J through M, wherein the liquid freshening composition has a vapor pressure at 25° C. of about 0.03 Torr to about 0.75 Torr.

O. The method of any of Paragraphs J through N, wherein the step of dispersing the liquid freshening composition further comprising dispersing the liquid freshening composition using an evaporative assistance element, wherein the evaporative assistance element is selected from the group consisting of: a heater, a fan, an agitator, and combinations thereof.

DETAILED DESCRIPTION OF THE DRAWINGS

Figure 4:
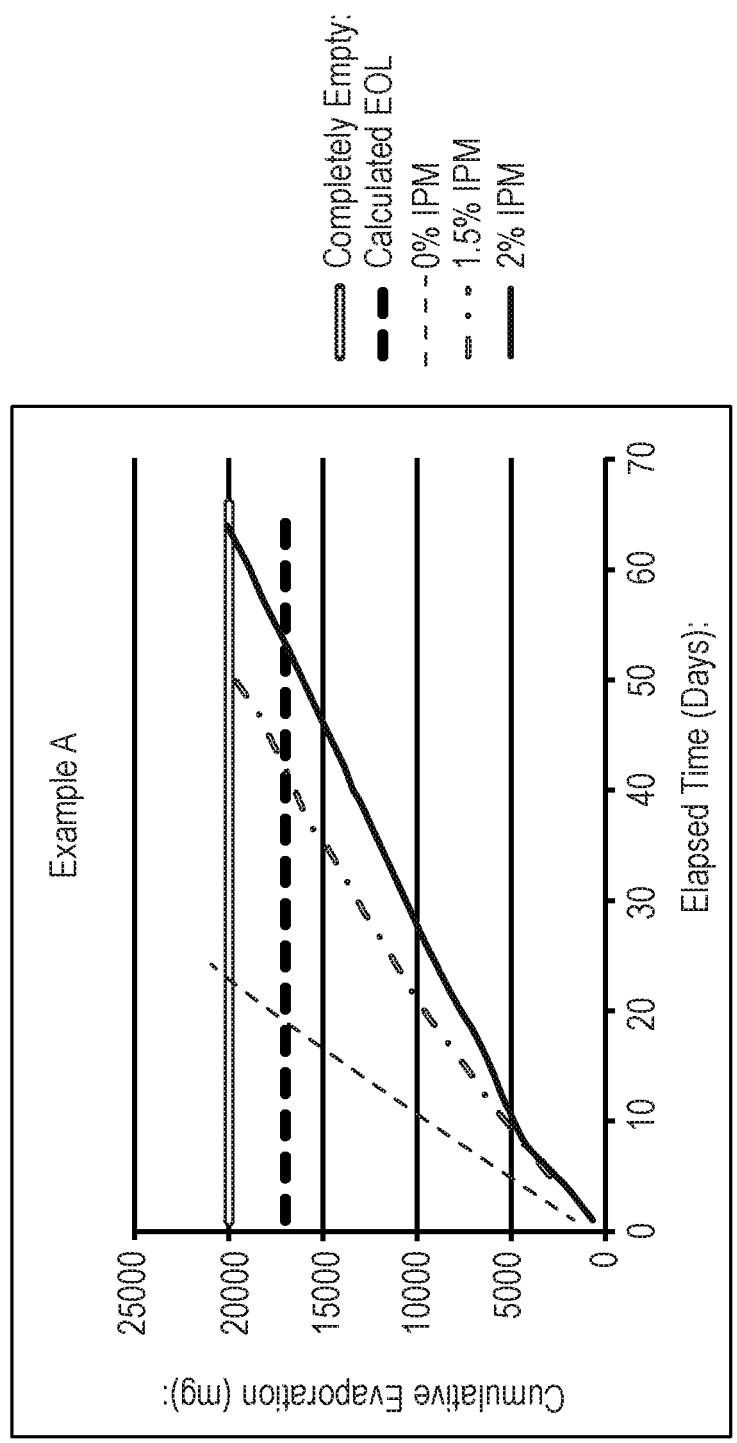

FIG. 4. is a graph of the evaporation of Example A.

Figure 5:
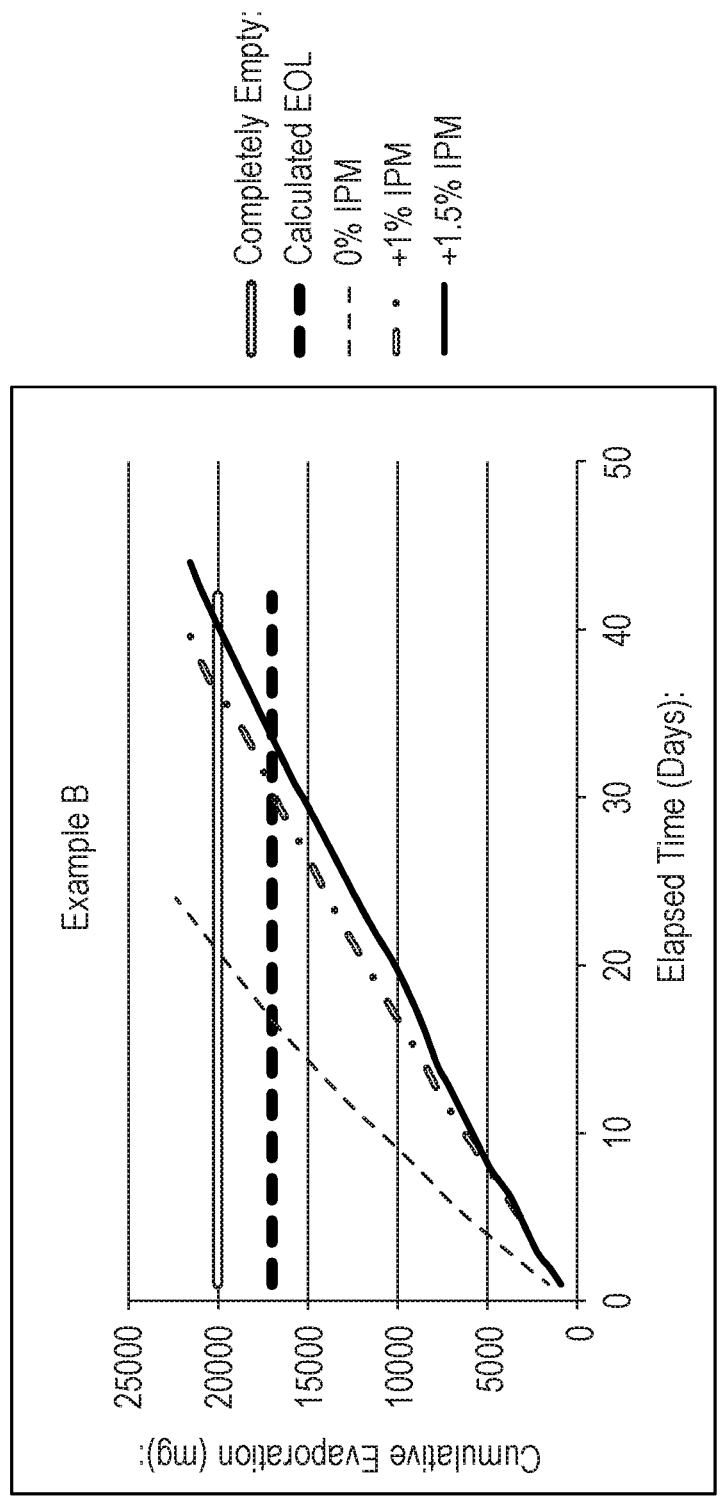

FIG. 5 is a graph of the evaporation of Example B.

Figure 6:
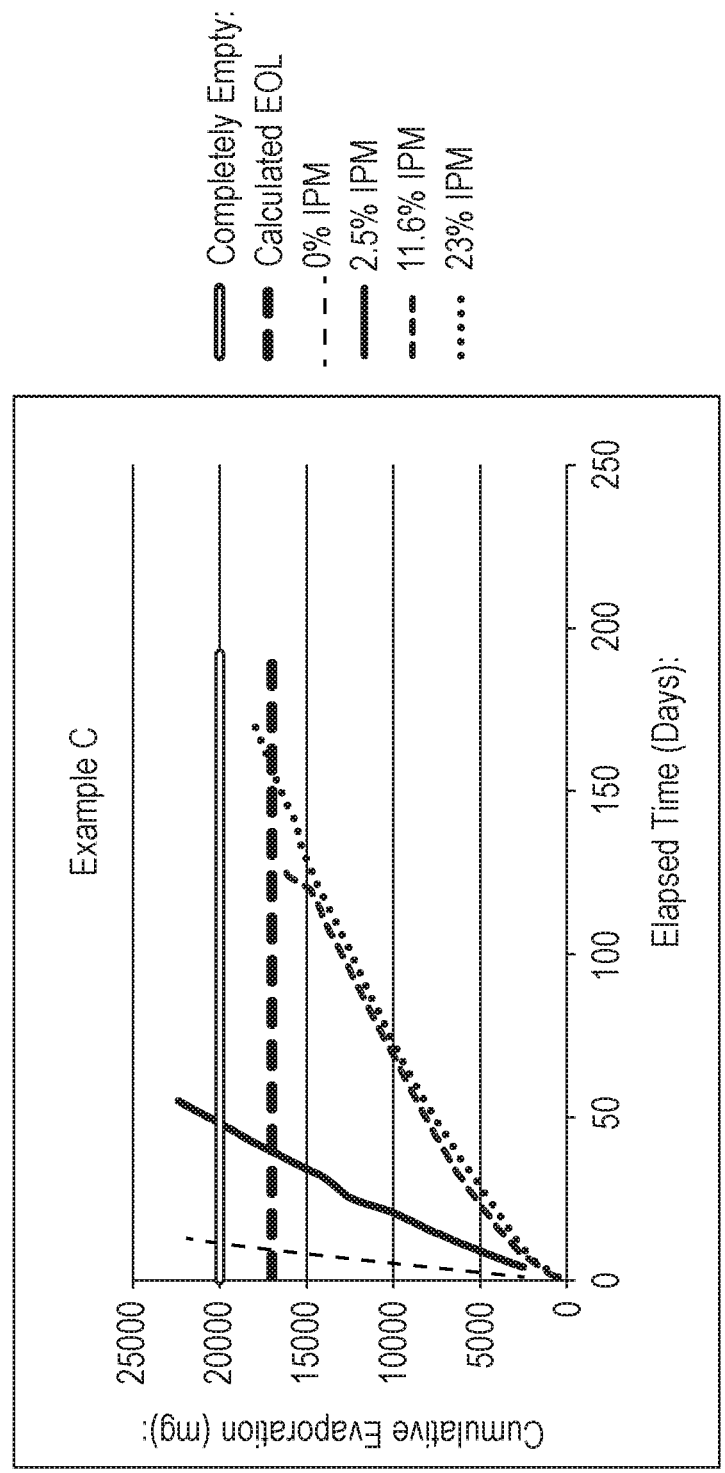

FIG. 6 is a graph of the evaporation of Example C.

Figure 7:
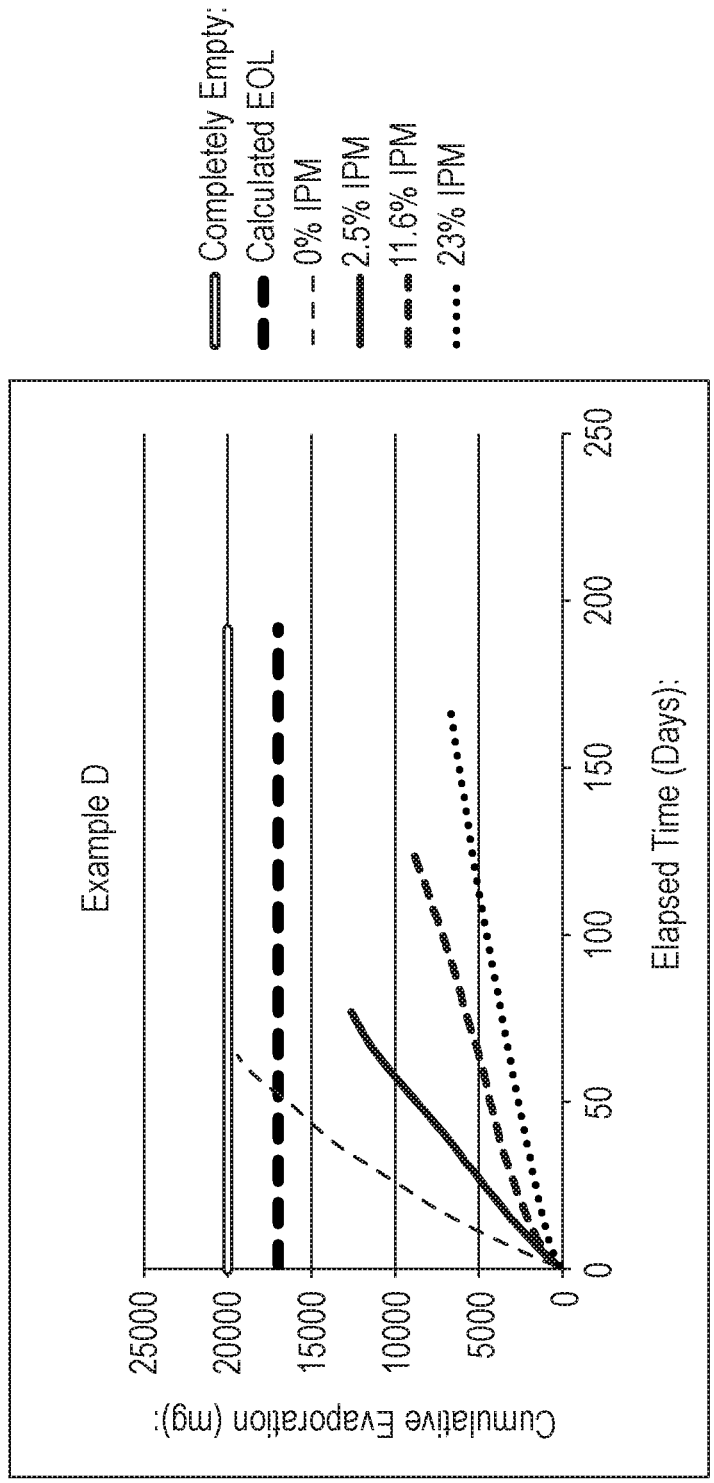

FIG. 7 is a graph of the evaporation of Example D.

Figure 8:
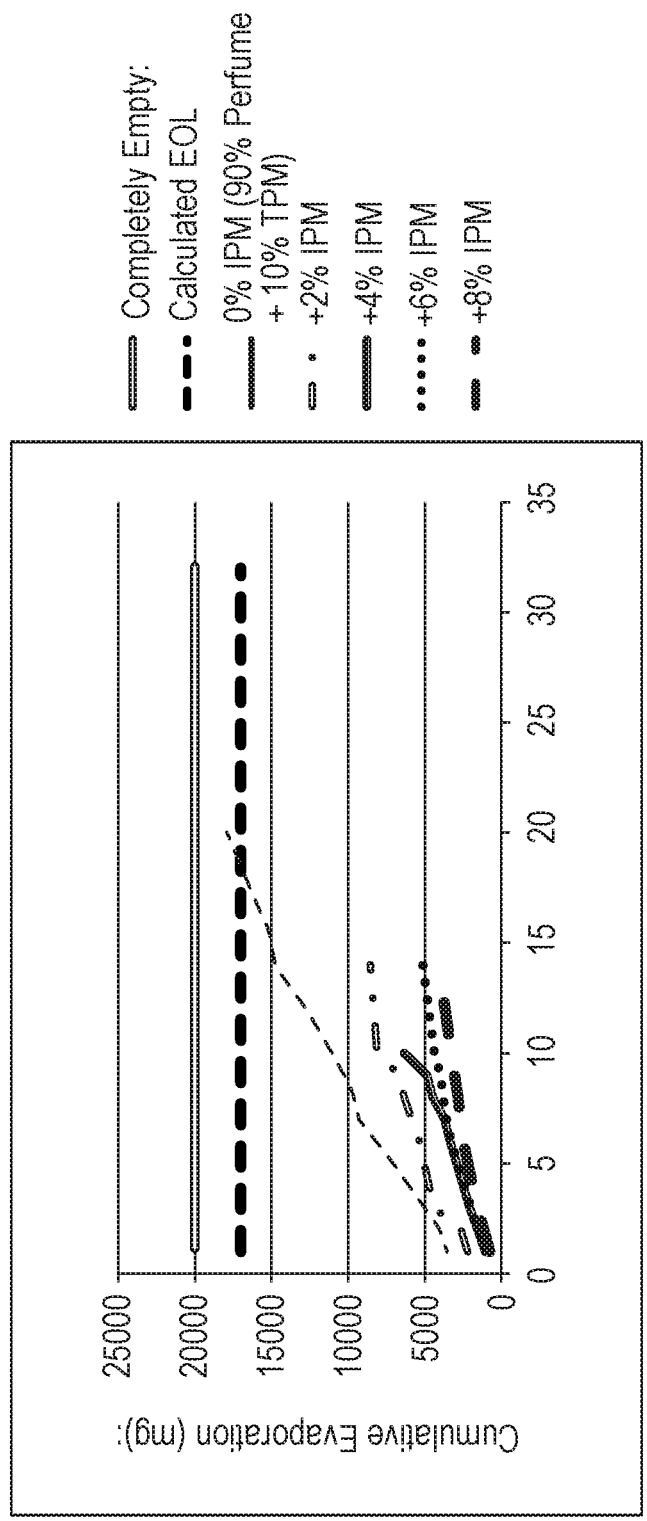

FIG. 8 is a graph of the evaporation of Example E.

DETAILED DESCRIPTION

The following definitions may be useful for understanding the present disclosure.

As used herein, "air care product" means products for treating or fragrancing the air including energized (i.e. electrically powered) air freshening delivery systems including fan-based diffusers, liquid electric pluggable air fresheners, electromechanical actuating diffusers; passive diffusers (i.e. not electrically powered) including membrane-based in-room air fresheners, car vent air fresheners As used herein, "freshening composition" means a composition that includes one or more perfume raw materials that is intended to treat (e.g. eliminate or reduce/minimize malodors), fragrance, and/or freshen the air. The freshening composition may be used with or without an air care product. Freshening compositions of the present invention include PRMs and may additionally include water, solubilizers, surfactants, diluents, malodor reducing actives, and perfume materials.

The perfume raw materials ("PRMs") disclosed, claimed and/or used in the perfume blends claimed and/or described herein encompass any stereoisomers of such PRMs.

Unless otherwise noted, all component or composition levels are in reference to the active portion of that component or composition, and are exclusive of impurities, for example, residual carriers or by-products, which may be present in commercially available sources of such components or compositions.

Freshening Composition

The freshening composition can be in a liquid form and can be a diffusive air freshener such as the liquid compositions used in FEBREZE® NOTICEables™ air freshener, AMBI PUR™ diffuser (single chamber & 3Volution), FEBREZE Car Vent Clips™ air freshener, or FEBREZE SMALL SPACES™ air freshener.

Freshening compositions have different evaporation rates depending on the volatility of the freshening composition. It has been found that a freshening composition comprising a low level of isopropyl myristate can drastically slow down the evaporation rate of a freshening composition, even highly volatile freshening compositions. Accordingly, air care products comprising the freshening composition are able to deliver long-lasting freshness using freshening compositions having a wide-range of vapor pressures.

The freshening composition may have a vapor pressure at 25° C. of about 0.03 Torr to about 1.0 Torr, alternatively about 0.1 Torr to about 0.75 Torr, alternatively about 0.1 Torr to about 0.60 Torr.

The freshening composition may have a viscosity of about 1.0 cP to less than about 25 cP, alternatively about 1.0 cP to less than about 23, alternatively about 1.0 cP to less than about 15 cP.

The freshening composition may be designed such that the composition may include a surface tension of about 19 mN/m to less than about 33 mN/m, alternatively about 19 mN/m to less than about 30 mN/m, alternatively about 19 mN/m to less than about 27 mN/m.

The freshening composition may be substantially free of volatile organic compounds ("VOCs"), meaning it has no more than about 18%, alternatively no more than about 6%, alternatively no more than about 5%, alternatively no more than about 1%, alternatively no more than about 0.5%, by weight of the composition, of VOCs. The composition may be free of VOCs.

Isopropyl Myristate

The freshening composition includes isopropyl myristate ("IPM") (IUPAC name: Propan-2-yl tetradecanoate, CAS No. 110-27-0), which is shown below as Formula I.

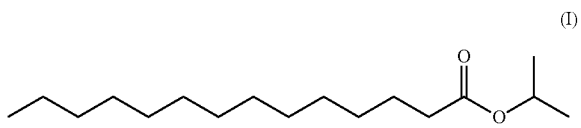 [SMILES: CCCCCCCCCCCCCC(=O)OC(C)C]

(I)

The freshening composition may comprise from about 0.5 wt. % to about 15 wt. %, alternatively about 0.50 wt. % to about 10.0 wt. %, alternatively about 0.50 wt. % to about 5.0 wt. %, alternatively about 0.75 wt. % to about 3.0 wt. %, alternatively about 1.0 wt. % to about 2.0 wt. % isopropyl myristate, by weight of the overall freshening composition.

Carrier

The freshening composition includes one or more carriers. The carrier may be selected from the group consisting of: a solvent, a diluent, a functional perfume component, or combinations thereof.

The carrier may be present in the freshening composition at a level of less than 70 wt. %, alternatively less than 60 wt. %, alternatively less than 50 wt. %, alternatively less than 40 wt. %, alternatively less than 30 wt. %, alternatively less than 20 wt. %, alternatively less than 15 wt. %, alternatively less than 10 wt. %, of the freshening composition.

The incorporation of a low level of isopropyl myristate may significantly reduce the level of carrier required to slow the evaporation rate of the freshening composition.

Solvent or Diluent

The carrier may include a solvent, diluent, or combinations thereof. The solvent or diluent may be selected from the group consisting of: dipropylene glycol methyl ether ("DPM"), tripropylene glycol methyl ether ("TPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether, and combinations thereof.

Functional Perfume Component

The carrier may include functional perfume components ("FPCs"). FPCs are a class of perfume raw materials with evaporation properties that are similar to traditional carriers or VOCs commonly used in air freshening compositions. The FPCs of the present invention aid in the evaporation of perfume raw materials and, in a mixture, provide a hedonic, fragrance benefit. FPCs may be used in relatively large concentrations without negatively impacting perfume character of the overall composition.

It has been understood that perfume raw material generates an olfactory response in the individual smelling the perfume. The minimum concentration of perfume ingredient which is consistently perceived to generate an olfactory response in an individual is known as the odor detection threshold ("ODT"). As the concentration of perfume is increased, so are the odor intensity of the perfume and the olfactory response of the individual. This continues until the concentration of the perfume reaches a maximum, at which point the odor intensity reaches a plateau beyond which there is no additional olfactory response by the individual. This range of perfume concentration through which the individual consistently perceives an odor is known as the Odor Detection Range ("ODR"). The concentration of perfume raw materials in a composition should be formulated less than or equal to the ODT or within the ODR of the perfume raw materials, since compositions comprising higher levels are costly and inefficient.

The Applicants have, however, found that in some circumstances it may be desirable to utilize FPCs that exceed the ODT, alternatively that exceed the ODR. Specifically, the use of these FPCs at higher levels than traditionally used in freshening compositions and without the presence of a traditional organic carriers, surprisingly, provides continuous fragrance to the atmosphere.

Perfume raw materials that are suitable as a FPC can be defined using Kovat's Index ("KI"). The KI places the volatility attributes of an analyte (e.g. component of a volatile composition) on a gas chromatography column in relation to the volatility characteristics of an n-alkane (normal alkane) series on that column. A typical gas chromatograph ("GC") column is a DB-5 column available from Agilent Technologies of Palo Alto, Calif. By this definition, the KI of a normal alkane is set to 100n, where n is the number of carbon atoms in the n-alkane. The KI of an analyte, x, eluting at time t', between two n-alkanes with number of carbon atoms "n" and "N" having corrected retention times t'n and ttN respectively, will then be calculated as:

On a non-polar to slightly polar GC stationary phase, KI of analytes are correlated with their relative volatility. For example, analytes with smaller KIs tend to be more volatile than those with larger KIs. Ranking analytes with their corresponding KI values gives a good comparison of analyte evaporation rates in liquid-gas partitioning systems.

A suitable FPC may have a Kovat's index from about 900 to about 1400, alternatively about 900 to about 1200, alternatively about 1000 to about 1100, alternatively about 1000.

Perfume raw materials that are suitable for use as a FPC can also be defined using ODT and non-polarizing scent character for a given perfume character scent camp. ODTs may be determined using a commercial gas chromatograph ("GC") equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability. The necessary amount of analyte is injected onto the column to achieve a 50 ppb concentration at the detector. Typical gas chromatograph parameters for determining odor detection thresholds are listed below. The test is conducted according to the guidelines associated with the equipment.

Equipment:

GC: 5890 Series with FID detector (Agilent Technologies, Ind., Palo Alto, Calif., USA)

7673 Autosampler (Agilent Technologies, Ind., Palo Alto, Calif., USA)

Column: DB-1 (Agilent Technologies, Ind., Palo Alto, Calif., USA)

Length 30 meters ID 0.25 mm film thickness 1 micron (a polymer layer on the inner wall of the capillary tubing, which provide selective partitioning for separations to occur)

Method Parameters:

Split Injection: 17/1 split ratio

Autosampler: 1.13 microliters per injection

Column Flow: 1.10 mL/minute

Air Flow: 345 mL/minute

Inlet Temp. 245° C.

Detector Temp. 285° C.

Temperature Information

Initial Temperature: 50° C.

Rate: 5 C/minute

Final Temperature: 280° C.

Final Time: 6 minutes

Leading assumptions: (i) 12 seconds per sniff (ii) GC air adds to sample dilution Suitable FPCs may have an ODT from greater than about 1.0 ppb, alternatively greater than about 5.0 ppb, alternatively greater than about 10.0 ppb, alternatively greater than about 20.0 ppb, alternatively greater than about 30.0 ppb, alternatively greater than about 0.1 parts per million ("ppm").

In addition to Kovat's and ODT properties mentioned above, other physical chemical properties of perfume raw materials that may render them useful as a FPC are molecular weight, vapor pressure, boiling point, flashpoint, heat of vaporization, viscosity, solubility parameters, and combinations of thereof.

Suitable FPCs may be highly volatile, low boiling, perfume ingredients. Exemplary FPC include iso-nonyl acetate, dihydro myrcenol (3-methylene-7-methyl octan-7-ol), linalool (3-hydroxy-3,7-dimethyl-1,6 octadiene), geraniol (3,7 dimethyl-2,6-octadien-1-ol), d-limonene (1-methyl-4-isopropenyl-1-cyclohexene), benzyl acetate, and combinations thereof.

Non-Functional Perfume Component

The freshening composition may include one or more non-functional perfume components. A non-functional perfume component is a perfume raw material ("PRM") that is utilized solely for its fragrance, scent, or hedonic benefits. Non-functional perfume components do not satisfy the properties of a functional perfume component. Suitable non-functional perfume raw materials are disclosed in U.S. Pat. Nos. 5,663,134; 5,670,475; 5,783,544; 5,939,060; and 6,146,621.

The freshening composition may include various different PRMs. Exemplary PRMs are listed in TABLE 1 below.

TABLE 1

Perfume Raw Materials

| CAS No. | Name |
|---|---|
|  | Lime Aldehyde |
| 1504-74-1 | Methoxycinnamaldehyde (Ortho) |
| 54082-68-7 | Onicidal (Muguet Undecadienal) |
| 1335-66-6 | Iso Cyclocitral |
| 16630-52-7 | 3-Methylthiobutanal |
| Specialty | Formyl Tricyclodecan Corps Iris |
| 120-14-9 | Corps 4322 (Vanillin Methyl Ether) |
| 93-08-3 | Methyl Beta Naphthyl Ketone |
|  | 6-Isopropyldecahydro-2-Naphtone |
| 123-69-3 | 8-Hexadecenolide |
|  | Eth-Me—Ph Glycidate Isomer |
| 1335-46-2 | Xandralia (Methyl) |
| Specialty | Hs Raspberry |
| Specialty | Berry Wescorps |
| Specialty | Cassis Base |
| 11245-8 | Undec-10-En-1-Al (10-Undecenal) |
| 41496-43-9 | 2-Methyl-3-Tolylproionaldehyde, 4-Dimethylbenzenepropanal (4-Dimethyl Benzenepropanal) |
|  | 4-Tricyclo5210-2,6decylidene-8butanal |
| 19009-56-4 | 2-Methyl Deca-1-Al (2 Methyl Decanal) |
| 55418-52-5 | Cassione (Heliotropin Acetone) |
| 100-06-1 | Para-Methoxy-Acetophenone |
| 10031-82-0 | 4-Ethoxybenzaldehyde |
| 100-51-6 | Benzyl Alcohol |
| 100-52-7 | Benzaldehyde |
| 10094-34-5 | Dimethyl Benzyl Carbinyl Butyrate |
| 101-39-3 | Alpha-Methyl Cinnamic Aldehyde |
| 101-39-3 | P-Methyl-Alpha-Pentylcinnamaldehyde |
| 101-39-3 | 2-Methyl 3-Phenyl Propenal |
| 101-39-3 | Methylcinnamaldehyde |
| 101-39-3 | Alpha-Methylcinnamaldehyde |
| 101-48-4 | Phenyl Acetaldehyde Dimethyl Acetal |
| 101-86-0 | Alpha-N-Hexyl-Cinnamaldehyde |
| 101-86-0 | 2-Hexyl 3-Phenyl Propenal |
| 101-86-0 | Hexyl Cinnamic Aldehyde |
| 101-86-0 | Jasmonal H |
| 101-86-0 | Alpha-Hexylcinnamaldehyde |
| 103-26-4 | Methyl Cinnamate |
| 103-48-0 | Phenyl Ethyl Iso-Butyrate |
| 103-54-8 | Cinnamyl Acetate |
| 103-60-6 | Phenoxy Ethyl Iso-Butyrate |
| 103-95-7 | Alpha-Methyl-P-Isopropyl Phenyl Propyl Aldehyde |
| 103-95-7 | Cymal |
| 103-95-7 | Cyclosal |
| 103-95-7 | Cyclamen Aldehyde |
| 103-95-7 | 2.Methyl-3(P-Isopropylphenyl)-Propionaldehyde |
| 103-95-7 | 3-(P-Isopropylphenyl)-Propionaldehyde |
| 104-09-6 | Syringaldehyde |
| 104-09-6 | P-Tolylacetaldehyde |
| 104-50-7 | Gamma-Octalactone |
| 104-53-0 | Benzenepropanal |
| 104-55-2 | Cinnamic Aldehyde |
| 104-67-6 | Undecalactone |
| 10486-19-8 | Tridecanal |
| 105-95-3 | Ethylene Brassylate |
| 106-02-5 | Pentadecanolide |
| 106-22-9 | Citronellol |
| 106-23-0 | 3,7-Dimethyl 6-Octenal |
| 106-23-0 | Citronellal |
| 106-24-1 | 3,7-Dimethyl-2,6-Octadien-1-Al |
| 106-26-3 | Neral |
| 106-72-9 | 2,6-Dimethyl-5-Heptenal |
| 106-72-9 | Melonal |
| 107-75-5 | 3,7-Dimethyl Octan-1-Al |
| 107-75-5 | Hydroxycitronellal |
| 107-75-5 | Citronellal Hydrate |

TABLE 1-continued

Perfume Raw Materials

| CAS No. | Name |
|---|---|
| 107-75-5 | 7-Hydroxy-3,7-Dimethyl Octan-1-Al |
| 107-86-8 | 3-Methyl-2-Butenal |
| 107898-54-4 | Polysantol |
| 108-29-2 | Gamma-Valero Lactone |
| 110-41-8 | 2-Methyl-1-Undecanal |
| 110-41-8 | Methyl Nonyl Acetaldehyde |
| 110-41-8 | Aldehyde C12 MNA |
| 110-62-3 | Pentanal |
| 110-62-3 | Valeraldehyde |
| 110-93-0 | Methyl-Heptenone |
| 111-30-8 | Glutaraldehyde |
| 111-30-8 | Pentanedial |
| 111-30-8 | Glutaric Aldehyde |
| 111-71-7 | Heptanal |
| 112-12-9 | Methyl Nonyl Ketone |
| 112-31-2 | Decanal |
| 112-44-7 | Undecenal |
| 112-54-9 | Lauric Aldehyde |
| 112-54-9 | 2-Dodecanal |
| 1128-08-1 | Dihydrojasmone |
| 115-95-7 | Linalyl Acetate |
| 116-26-7 | 2,6,6-Trimethyl-1,3-Diene Methanal |
| 116-26-7 | Safranal |
| 118-58-1 | Benzyl Salicylate |
| 1191-16-8 | Prenyl Acetate |
| 1192-88-7 | 1-Cyclohexene-1-Carboxaldehyde |
| 119-36-8 | Methyl Salicylate |
| 1195-79-5 | Fenchone |
| 119-61-9 | Benzophenone |
| 120-14-9 | 3,4-Dimethoxybenzaldehyde |
| 120-14-9 | Veratraldehyde |
| 120-51-4 | Benzyl Benzoate |
| 1205-17-0 | 2-Methyl-3-(3,4-Methylenedioxyphenyl)Propanal |
| 1205-17-0 | Helional |
| 120-57-0 | 3,4-Methylene Dioxy Benzaldehyde |
| 120-57-0 | Heliotropin |
| 120-72-9 | Indole |
| 121-32-4 | 3-Ethoxy 4-Hydroxybenzaldehyde |
| 121-32-4 | Ethyl Vanillin |
| 121-33-5 | Vanillin |
| 122-00-9 | Methyl-Acetophenone |
| 122-03-2 | 4-Isopropyl Benzaldehyde |
| 122-03-2 | Cuminaldehyde |
| 122-40-7 | Amyl Cinnamic Aldehyde |
| 122-40-7 | Alpha-Amylcinnamic Aldehyde |
| 122-40-7 | 2-Pentyl-3-Phenylpropenoic Aldehyde |
| 122-48-5 | 4-(4-Hydroxy-3-Methoxyphenyl)-2-Butanone |
| 122-78-1 | Phenylacetaldehyde |
| 122-97-4 | Phenyl Propyl Alcohol |
| 123-11-5 | P-Methoxybenzene Aldehyde |
| 123-11-5 | Anisic Aldehyde |
| 123-11-5 | Anisaldehyde |
| 123-15-9 | 2-Methyl Valeraldehyde |
| 123-15-9 | 2-Methylpentanal |
| 123-38-6 | Propanal |
| 123-38-6 | Propionaldehyde |
| 123-68-2 | Allyl Caproate |
| 123-72-8 | Butyraldehyde |
| 124-13-0 | Octanal |
| 124-19-6 | Nonanal |
| 125109-85-5 | 3-(3-Isopropyl-Phenyl)-Butyraldehyde |
| 125109-85-5 | Florhydral |
| 127-41-3 | Alpha-Ionone |
| 127-42-4 | Alpha-Methyl Ionone |
| 127-43-5 | N-Beta-Methyl Ionone Isomer |
| 127-51-5 | Gamma-Methyl Ionone |
| 128-37-0 | BHT |
| 1322-58-3 | Tetrameran |
| 1335-66-6 | Iso-Cyclo Citral |

TABLE 1-continued

Perfume Raw Materials

| CAS No. | Name |
|---|---|
| 1335-66-6 | 2,4,6-Trimethyl-3-Cyclohexene-1-Carboxaldehyde |
| 1335-66-6 | Iso Cyclocitral |
| 1337-83-3 | Intreleven Aldehyde |
| 134-96-3 | 3,5-Dimethoxy 4-Hydroxybenzaldehyde |
| 137-03-1 | Fleuramone |
| 139-85-5 | 3,4-Dihydroxybenzaldehyde |
| 139-85-5 | Catechaldehyde |
| 140-11-4 | Benzyl Acetate |
| 141-13-9 | 2,6,10-Trimethyl-9-Undecenal |
| 141-13-9 | Adoxal |
| 141773-73-1 | Helvetolide |
| 142-83-6 | 2,4-Hexadienal |
| 14371-10-9 | Phenyl Propenal, 3-Phenyl-2-Propenal |
| 14765-30-1 | Freskomenthe |
| 14901-07-6 | Beta-Ionone |
| 14901-07-6 | Ionone Beta |
| 151-05-3 | Dimethyl Benzyl Carbinyl Acetate |
| 15764-16-6 | 2,4-Dimethylbenzaldehyde |
| 16251-77-7 | Trifernal |
| 16251-77-7 | 3-Phenyl Butanal |
| 16587-71-6 | Orivone |
| 17283-81-7 | Dihydro-Beta-Ionone |
| 1728-46-7 | Verdone |
| 173445-65-3 | Neo Hivernal |
| 18127-01-0 | 4-T-Butylbenzenepropionaldehyde |
| 18127-01-0 | Bourgeonal |
| 18479-58-8 | Dihydro Myrcenol |
| 18829-55-5 | Trans Heptenal |
| 18829-56-6 | Nonenal |
| 19009-56-4 | Methyl Octyl Acetylaldehyde |
| 19009-56-4 | Aldehyde C-11 MOA |
| 20407-84-5 | Mandarine Aldehyde |
| 20407-84-5 | Mandarinal |
| 20665-85-4 | Vanillin Isobutyrate |
| 2111-75-3 | L-4(1-Methylethenyl)-1-Cyclohexene-1-Carboxaldehyde |
| 2111-75-3 | Perillaldehyde |
| 21145-77-7 | Tonalid |
| 21145-77-7 | Musk Plus |
| 21944-98-9 | Tangerinal |
| 22471-55-2 | Thesaron |
| 2349-07-7 | Hexyl Iso-Butyrate |
| 23696-85-7 | Damascenone |
| 98-86-2 | Acetophenone |
| 24048-13-3 | 2,6,10-Trimethyl-5,9-Undecadien-1-Al |
| 24680-50-0 | Trans-4-Methoxycinnamaldehyde |
| 24851-98-7 | Methy-Dihydrojasmonate |
| 24851-98-7 | Hedione |
| 24851-98-7 | Methyl Dihydro Jasmonate |
| 25152-84-5 | 2,4-Decadienal |
| 2548-87-0 | Octenal |
| 2550-11-0 | Dimethyl-Octenone |
| 2550-26-7 | Benzyl-Acetone |
| 26370-28-5 | 2,6-Nonadienal |
| 27939-60-2 | Trivertal |
| 29214-60-6 | Gelsone |
| 30168-23-1 | Duplical |
| 30168-23-1 | Tricyclodecylidenebutanal |
| 30361-28-5 | 2,4-Octadienal |
| 30772-79-3 | Melozone |
| 31375-17-4 | 1-(P-Menthen-6(2)-Yl)-1-Propanone |
| 31906-04-4 | 4-(4-Hydroxy-4-Methyl Pentyl)-3-Cyclohexene-1-Carboxaldehyde |
| 31906-04-4 | Cyclohexenyl-Carboxaldehyde |
| 32210-23-4 | 4-Tertiary Butyl Cyclohexyl Acetate |
| 32210-23-4 | Vertenex |
| 32388-55-9 | Methyl-Cedrenyl-Ketone |
| 32388-55-9 | Methyl Cedrylone Major |
| 32388-55-9 | Methyl-Cedrylone |
| 33704-61-9 | Musk Indanone |
| 33704-61-9 | 6,7-Dihydro-1,1,2,3,3-Pentamethyl-4(5h)-Indanone |
| 33885-51-7 | Pino Acetaldehyde |
| 34590-94-8 | Dowanol DPM Isomer |
| 34902-57-3 | Habanolide |
| 35044-59-8 | Ethyl Safranate |
| 35044-68-9 | Beta-Damascone |
| 35044-68-9 | Damascone Beta |
| 35158-25-9 | 2-Isopropyl-5-Methyl-2-Hexenal |
| 36306-87-3 | 4-(1-Ethoxyvinyl)-3,3,5,5,-Tetramethyl-Cyclohexanone |
| 3720-16-9 | Celery Ketone |
| 3720-16-9 | Livescone |
| 37609-25-9 | 5-Cyclohexadecenone |
| 37677-14-8 | Myrac Aldehyde |
| 39255-32-8 | Manzanate |
| 39255-32-8 | Ethyl 2 Methyl Pentanoate |
| 41496-43-9 | Jasmorange |
| 41496-43-9 | Satinaldehyde |
| 41724-19-0 | Plicatone |
| 42370-07-0 | 2-Acetyl-3,3-Dimethyl-Norbornane |
| 43052-87-5 | Damarose Alpha |
| 43052-87-5 | Alpha-Damascone |
| 432-25-7 | Beta-Cyclocitral |
| 4411-89-6 | 2-Phenyl 2-Butenal |
| 4411-89-6 | Phenyl Butenal |
| 4433-36-7 | 3,4,5,6-Tetrahydropseudoionone |
| 470-82-6 | Eucalyptol |
| 472-66-2 | 2,6,6-Trimethyl-1-Cyclohexene-1-Acetaldehyde |
| 472-66-2 | B-Homocyclocitral |
| 4748-78-1 | 4-Ethyl Benzaldehyde |
| 4819-67-4 | Delphone |
| 488-10-8 | Cis-Jasmone |
| 491-35-0 | Lepidine |
| 4927-36-0 | 4-Damascol |
| 4940-11-8 | Ethyl Maltol |
| 495-85-2 | Amylaldehyde |
| 502-72-7 | Cyclopentadecanone |
| 51414-25-6 | Lyral |
| 52474-60-9 | Precyclemeone B |
| 5392-40-5 | Citral |
| 5392-40-5 | Geranial |
| 541-91-3 | Muscone |
| 54464-57-2 | Iso-E-Super |
| 54464-57-2 | Isocyclemone E |
| 5462-06-6 | Canthoxal |
| 5462-06-6 | Anisylpropanal |
| 5471-51-2 | Para Hydroxy Phenyl Butanone |
| 55066-49-4 | 3-Methyl-5-Phenyl Pentanal |
| 55066-49-4 | Mefranal |
| 55418-52-5 | Dulcinyl |
| 564-94-3 | Myrtenal |
| 564-94-3 | Pin-2-Ene-1-Carbaldehyde |
| 56973-85-4 | Neobutenone |
| 5703-26-4 | 4-Methylphenylacetaldehyde |
| 57378-68-4 | Delta-Damascone |
| 57934-97-1 | Givescone |
| 58430-94-7 | Iso-Nonyl Acetate |
| 590-86-3 | 3-Methyl Butyraldehyde |
| 590-86-3 | Isovaleraldehyde |
| 59323-76-1 | Oxane |
| 5988-91-0 | Dihydrocitronellal |
| 5989-27-5 | D-Limonene |
| 60-12-8 | Phenyl Ethyl Alcohol |
| 613-69-4 | 2-Ethoxybenzaldehyde |
| 621-59-0 | 4-Methoxy 3-Hydroxy Benzaldehyde |
| 623-36-9 | 2-Methyl-2-Pentenal |
| 623-36-9 | 2-Methylpentenal |
| 62439-41-2 | Methoxy Melonal |
| 62439-41-2 | 6-Methoxy-2,6-Dimethylheptanal |
| 62518-65-4 | Mefloral |
| 62518-65-4 | Lilestralis 33 |
| 628-63-7 | Amyl-Acetate |
| 6413-10-1 | Fructone |

TABLE 1-continued

Perfume Raw Materials

| CAS No. | Name |
|---|---|
| 65443-14-3 | Veloutone |
| 65885-41-8 | Beta Methyl Benzenepropanal |
| 659-70-1 | Iso-Amyl Iso-Valerate |
| 66-25-1 | Hexenal |
| 66327-54-6 | 1-Methyl-4-(4-Methylpentyl)-3-Cyclohexenecarbaldehyde |
| 66327-54-6 | Vernaldehyde |
| 6728-26-3 | 2-Hexenal |
| 6728-31-0 | Cis Heptenal |
| 6753-98-6 | Alpha-Caryophyllene |
| 67633-95-8 | Methyl-Lavender-Ketone |
| 67634-14-4 | Para-Ethyl-Alpha, Alpha-Dimethyl Hydrocinnamaldehyde |
| 67634-14-4 | Floralozone |
| 67801-65-4 | Triplal Extra |
| 67845-30-1 | Maceal |
| 68039-49-6 | 2,4-Dimethyl-3-Cyclohexene-1-Carboxaldehyde |
| 68039-49-6 | Cyclal C |
| 68039-49-6 | Ligustral |
| 68039-49-6 | Triplal |
| 99-49-0 | Carvone |
| 68039-49-6 | Vertocitral |
| 68039-49-6 | 2,4-Dimethyl-3-Cyclohexen-1-Carbaldehyde |
| 68480-14-8 | Methyl Cyclocitrone |
| 68737-61-1 | 2,4-Dimethylcyclohex-3-Ene-1-Carbaldehyde |
| 68738-96-5 | Cyclemone A |
| 68912-13-0 | Frutene |
| 68991-97-9 | Melafleur |
| 68991-97-9 | 1,2,3,4,5,6,7,8-Octahydro-8,8-Dimethyl-2-Naphthaldehyde |
| 70266-48-7 | Iso-Damascone |
| 706-14-9 | Gamma Decalactone |
| 71077-31-1 | Floral Super |
| 74338-72-0 | 2,4,4,7-Tetramethyl-Oct-6-En-3-One |
| 7452-79-1 | Ethyl-2-Methyl Butyrate |
| 74568-05-1 | Gamma Undecalactone |
| 7492-67-3 | 3,7-Dimethyl-6-Octenyl Oxyacetaldehyde |
| 7492-67-3 | Citronellyl Oxyacetaldehyde |
| 7492-67-3 | Muget Aldehyde 50 |
| 75-07-0 | Ethanal |
| 75-07-0 | Acetaldehyde |
| 75147-23-8 | Buccoxime |
| 76-22-2 | Camphor |
| 7775-00-0 | Cyclemax |
| 78-70-6 | Linalool |
| 78-84-2 | Isobutyraldehyde |
| 78-98-8 | Pyruvaldehyde |
| 79-76-5 | Gamma-Ionone |
| 79-78-7 | Hexalon |
| 8028-48-6 | Orange Oil Tarocco |
| 80-54-6 | 2-Methyl-4-T-Butylphenyl)Propanal |
| 80-54-6 | 4-Tert-Butyl-Alpha-Methyl-Hydrocinnamaldehyde |
| 80-54-6 | Lilial |
| 80-54-6 | P.T. Bucinal |
| 80-54-6 | Lysmeral |
| 98-53-3 | Para-Tert-Butyl-Cyclohexanone |
| 80-56-8 | Alpha-Pinene |
| 81782-77-6 | Undecavertol |
| 82461-14-1 | Rhubafuran |
| 84697-09-6 | Acalea |
| 85-91-6 | Dimethyl Anthranilate |
| 86803-90-9 | Scentenal |
| 86803-90-9 | Octahydro-5-Methoxy-4,7-Methano-1H-Indene-2-Carboxaldehyde |
| 88-41-5 | Verdox Major |
| 88-41-5 | Verdox |
| 89-80-5 | Menthone |
| 90-02-8 | 2-Hydroxy Benzaldehyde |
| 90-02-8 | Salicylaldehyde |
| 90105-92-3 | Prunella |
| 90-87-9 | Hydrotropaldehyde |
| 91462-24-7 | Cyclic Ethylene Dodecanedioate |
| 91-64-5 | Coumarin |
| 928-96-1 | Beta-Gamma Hexenol |
| 93-08-3 | Methyl-Beta-Naphthyl-Ketone |
| 93-16-3 | Methyl Isoeugenol |
| 93-28-7 | Eugenyl Acetate |
| 93-53-8 | 2-Phenylproprionaldehyde |
| 93-92-5 | Methyl Phenyl Carbinyl Acetate |
| 95-41-0 | Iso Jasmone |
| 95962-14-4 | 2-(2-(4-Methyl-3-Cyclohexen-1-Yl)Propyl)-Cyclopentanone |
| 96-17-3 | 2-Methyl Butyraldehyde |
| 96-17-3 | Methylbutyraldehyde |
| 97-53-0 | Eugenol |
| 97-96-1 | 2-Ethylbutyraldehyde |

The freshening composition may comprise from greater than 10 wt. %, alternatively greater than 20 wt. %, alternatively greater than 30 wt. %, alternatively greater than 40 wt. %, alternatively greater than 50 wt. %, alternatively greater than 60 wt. %, alternatively greater than 70 wt. %, alternatively greater than 85 wt. %, of perfume raw materials, based on the total weight of the freshening composition.

Active Agents

The freshening composition may include an active agent. Active agents provide cleaning, surface care protection, fabric conditioning or softening, fabric refreshing, de-wrinkling, air freshening, air deodorizing, malodor removal, skin moisturizing, body deodorizing, or like benefits. An active agent does not include water or deionized water.

In a freshening composition, the active agents may deliver a genuine malodor removal benefit. A genuine malodor removal benefit is defined as both a sensory and analytically measurable (such as by GC) malodor reduction. Thus, if the air freshening composition delivers a genuine malodor removal benefit, the air freshening composition will not function merely by using perfume to cover up or mask odors. If the air freshening product is provided with a malodor controlling agent, the air freshening product may utilize one or more of several types of odor control mechanisms. One suitable malodor controlling agent is cyclodextrin.

Active agents might also include surfactants, emulsifiers, solubilizers, polymers, malodor counteractants such as cyclodextrin, hydrogen peroxide, buffers, zinc ions, etc.

Air Care Product

The freshening composition may be used with an air care product to deliver the non-functional perfume raw materials to the atmosphere and/or a surface. It is contemplated that the air care product may be configured for use in a variety of applications to deliver volatile materials to the atmosphere and/or a surface.

For example, the air care product may be configured as an energized device. An exemplary energized device may be an electrical device. The energized device may be an electrical wall plug or battery operated air freshener having a delivery engine, such as a wick, that is used to transport a freshening composition and/or evaporate a freshening composition therefrom; or other heating devices (e.g. devices powered by chemical reactions such as catalyst fuel systems; solar powered devices, etc.). In such devices, the delivery engine is designed to transport a freshening composition and/or evaporate a freshening composition therefrom. The energized device may also include a microfluidic die having either a heater(s) or piezo crystal(s) that are used to dispense droplets of the freshening composition into the air.

When the delivery engine is used to evaporate the freshening composition therefrom, the delivery engine may be placed next to one or more evaporative assistance elements, such as a heater, to disperse the freshening composition in the atmosphere.

The delivery engine may be configured in various ways. For example, the delivery engine may be in the form of a wick, membrane, gel, porous or semi-porous substrate, including a felt pad.

If the air freshener product includes a delivery engine in the form of a wick, the wick may be configured to have various different shapes and sizes. For example, the wick may have a cylindrical or an elongate cube shape. The wick may be defined by a length and a diameter or width, depending on the shape. The wick may have various lengths. For example, the length of the wick may be in the range of about 1 millimeter ("mm") to about 100 mm, or from about 5 mm to about 75 mm, or from about 10 mm to about 50 mm. The wick may have various diameters or widths. For example, diameter or width of the wick may be at least 1 mm, or at least 2 mm, or at least 3 mm, or at least 4 mm.

A wick may exhibit a density. The wick density may be in the range of about 0.100 grams/cm$^3$ ("g/cc") to about 1.0 g/cc.

A wick may comprise a porous or semi-porous substrate. The wick may be composed of various materials and methods of construction, including, but not limited to, bundled fibers which are compressed and/or formed into various shapes via overwrap (such as a non-woven sheet overwrap) or made of sintered plastics such as PE, HDPE or other polyolefins. For example, the wick may be made from a plastic material such as polyethylene or a polyethylene blend.

Instead of evaporating the freshening composition from the delivery engine, the delivery engine may transport the freshening composition to a microfluidic die or an evaporative surface. For example, the delivery engine may transport the fluid composition, through capillary action, to a microfluidic die that uses a heater or piezo crystal to atomize or disperse droplets of the freshening composition into the atmosphere.

The evaporative surface may be integral or separate from the evaporative assistance element and/or the delivery engine. The evaporative surface may be configured as a porous or semi-porous substrate, a bowl or plate, including a plastic, glass, or metal bowl or plate, and combinations thereof.

When an evaporative assistance element is used, the evaporative assistance element may be configured in various ways. The evaporative assistance element may be used to achieve the evaporation of a freshening composition from an air care product. For example, the evaporative assistance element may be selected from the group consisting of a heater, a fan, an agitation member or agitator, both powered agitator and manual agitator, or combinations thereof. The evaporative assistance element may also include a heating element to heat the liquid volatile composition, a chemical constituent to speed evaporation or release rates, use of a chemically heated membrane to provide increased evaporation via exothermic reaction, or synergistic combinations thereof.

An energized device having an evaporative assistance element in the form of a heater may be configured to heat the delivery engine to various temperatures. For example, the energized device may be configured such that the heater heats the evaporative surface, such as a wick, membrane, gel, porous or semi-porous substrate such as a felt pad, to a temperature of about 30° C. to about 150° C. An energized device may include a control system such that the heater temperature is adjustable. The control system may also cycle the heater temperature to have greater control over the evaporation of the freshening composition.

Figure 1A:
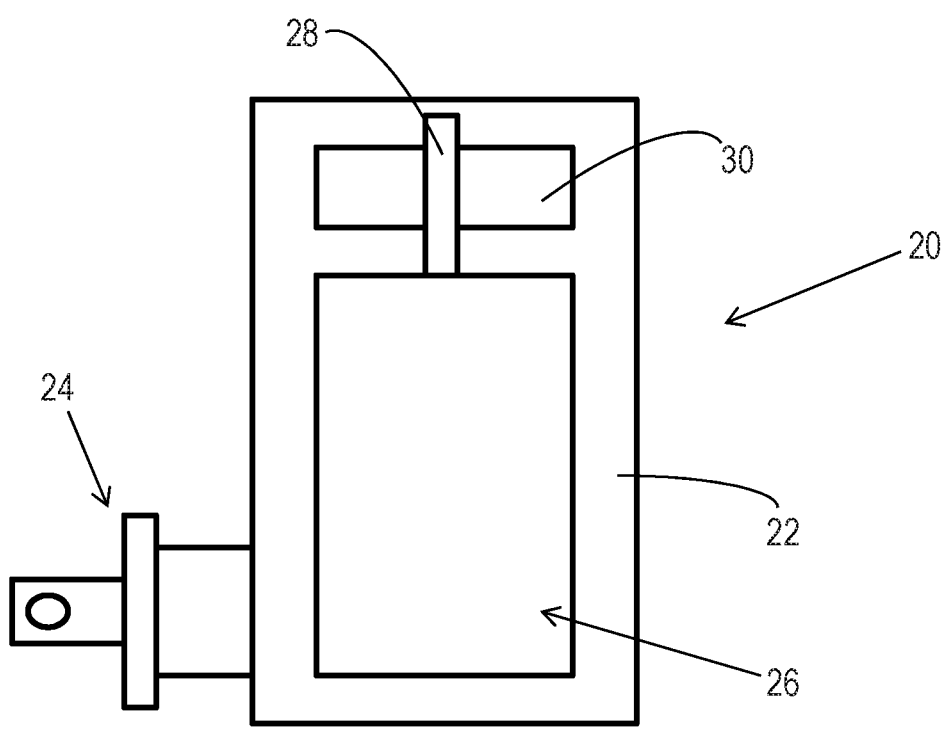
FIG. 1A is a schematic of an exemplary air care product in the form of an electrical wall plug air freshener.

An exemplary energized device is shown in FIG. 1A in the form of an electrical wall plug air freshener 20. The wall plug air freshener 20 may include a housing 22, and the housing 22 is supported on an electrical outlet by a plug 24 that is at least indirectly joined to the housing 22. The air freshener 20 further comprises at least one reservoir 26 for containing the freshening composition. The housing 22 may serve as a holder for the reservoir(s) and any of the other components of the air freshener. The air freshener comprises a delivery engine in the form of a wick 28 and an evaporative assistance element in the form of a heater 30 for dispensing the volatile material. While FIG. 1A illustrates one reservoir, one evaporative assistance element, and one delivery engine, it is to be appreciated that the air freshener may include more than one reservoir, evaporative assistance element, and/or delivery engine. If the air freshener includes more than one reservoir, each reservoir may contain a different freshening composition or may contain the same freshening composition.

Figure 1B:
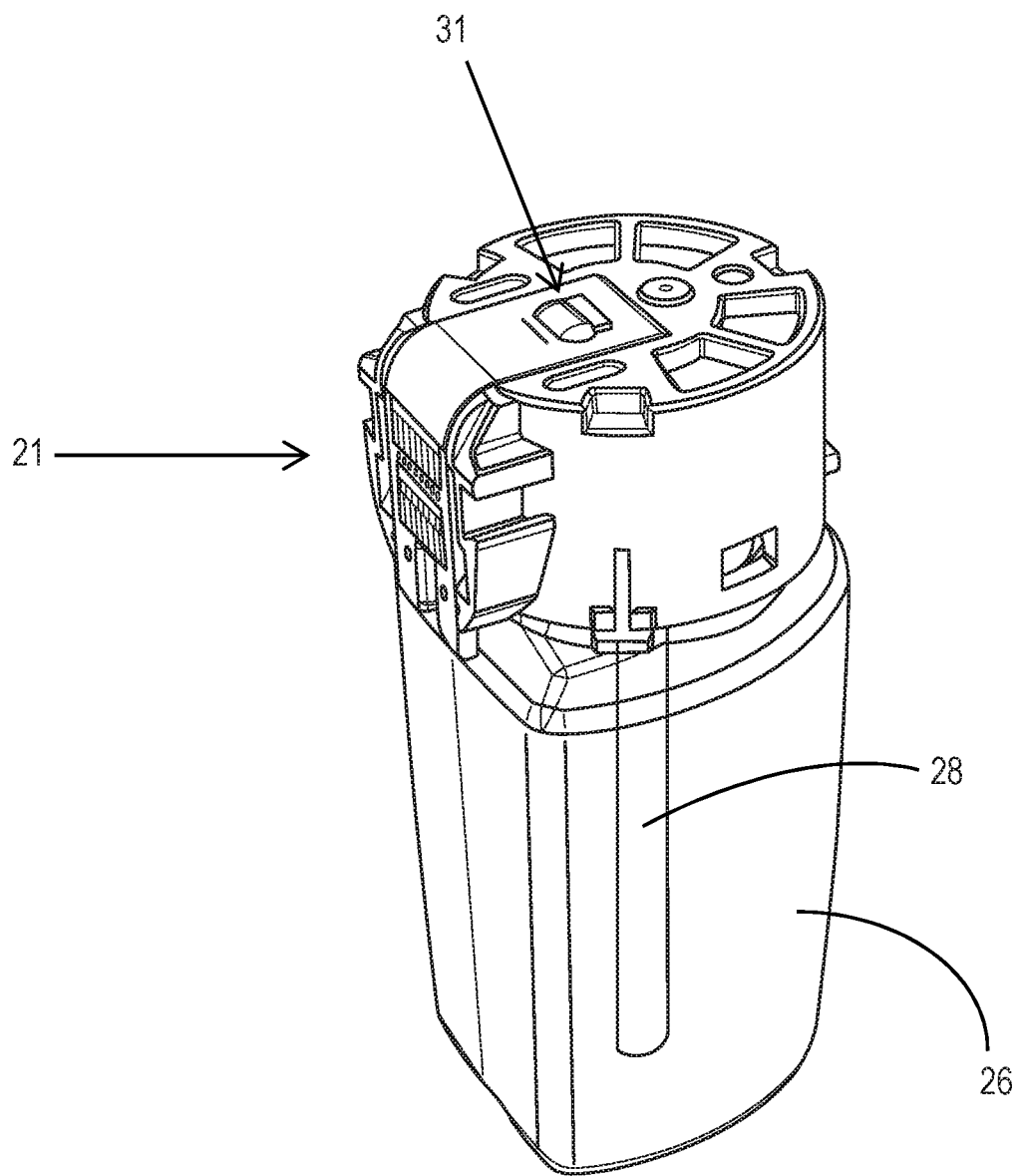
FIG. 1B is a perspective view of an exemplary cartridge of an air care product having a microfluidic die and a wick that delivers the freshening composition to the microfluidic die.

FIG. 1B illustrates a cartridge 21 of an exemplary air care product comprising a microfluidic die. A cartridge 21 comprising a microfluidic die, such as shown in FIG. 1B, may include a reservoir 26 for containing the freshening composition, a delivery engine in the work of a wick 28 that is in fluid communication with the reservoir 26 and the freshening composition contained with the reservoir 26, and a microfluidic die 31. The microfluidic die 31 may include a heater(s) or piezo crystal(s) that is used to atomization the freshening composition to dispense the freshening composition into the atmosphere. The cartridge may be connected with a housing that supplies electricity to the microfluidic die 31.

The air care product may also be configured as a passive air diffuser apparatus that includes a breathable membrane for diffusing freshening composition.

Figure 2:
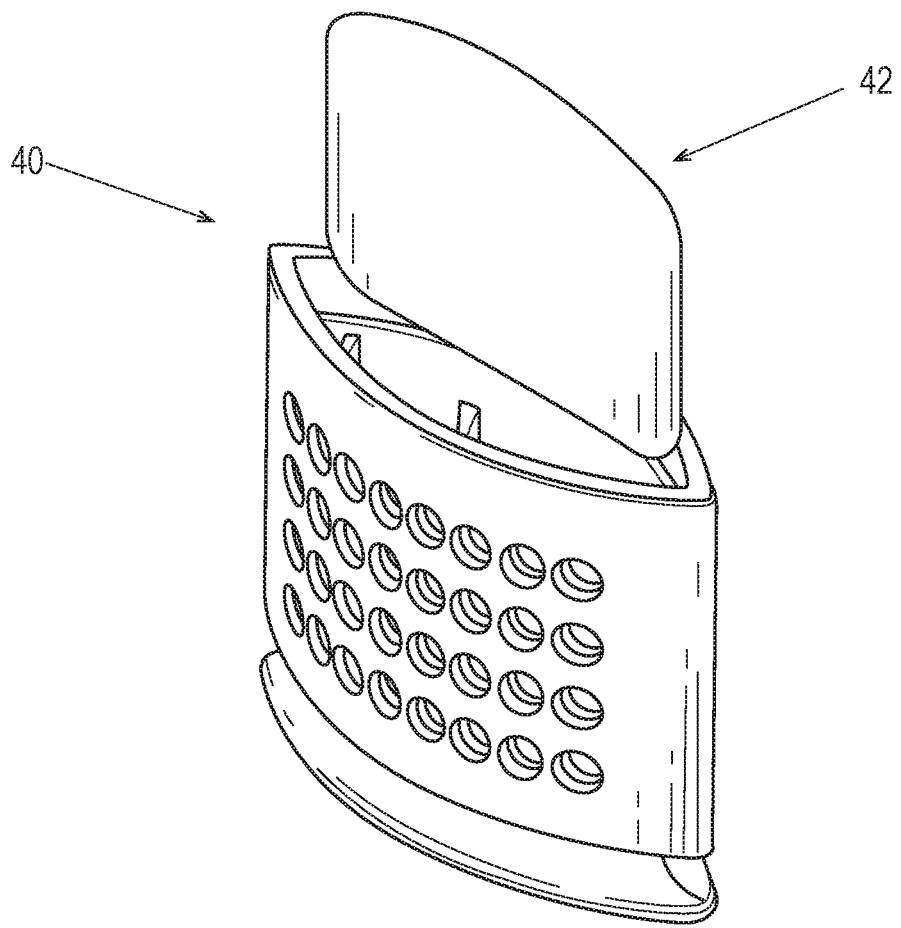
FIG. 2 is a perspective view of an exemplary passive air care product having a breathable membrane.
Figure 3:
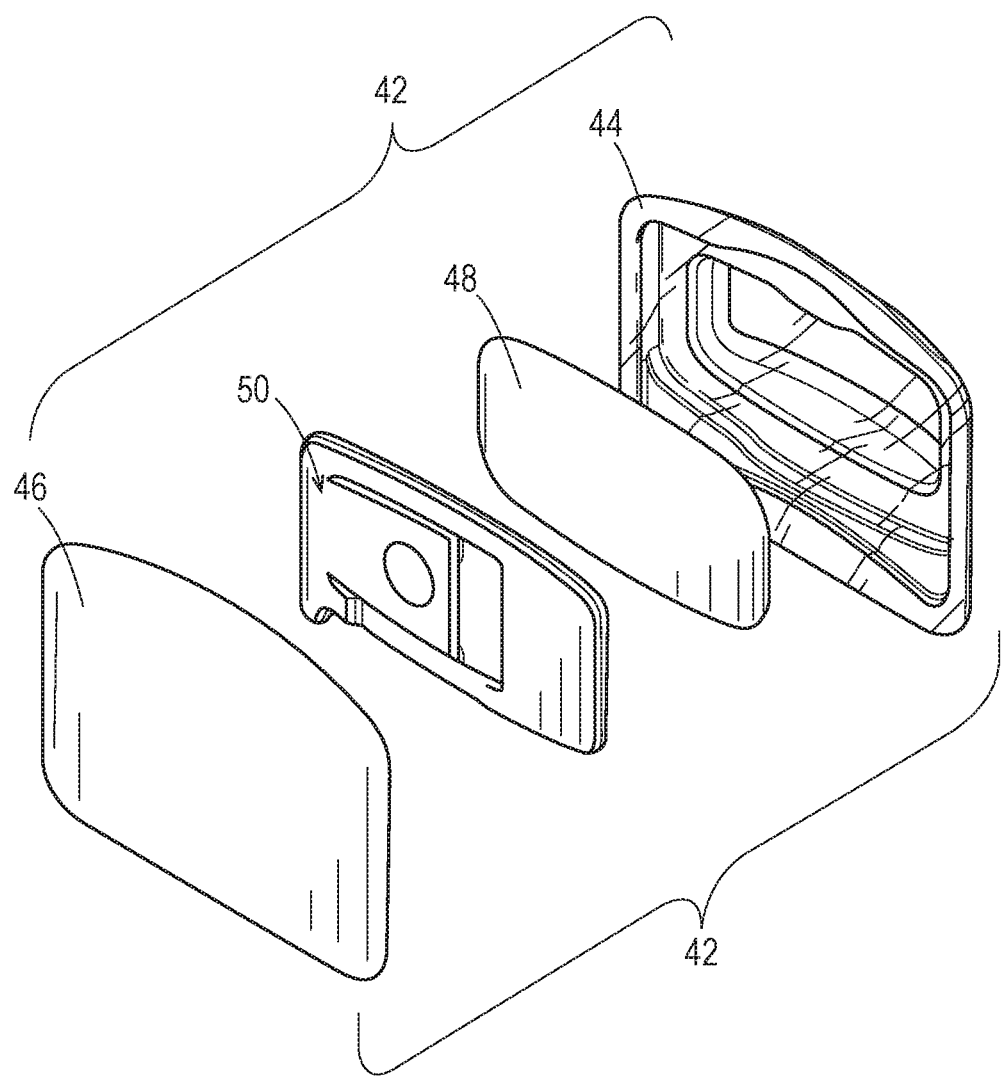
FIG. 3 is an exploded view of an exemplary passive air care product having a breathable membrane.

For example, as shown in FIGS. 2 and 3, the apparatus 40 for delivering a freshening composition may comprise a delivery engine 42 having a liquid reservoir 44 for containing a freshening composition and a breathable membrane 46 enclosing the liquid reservoir 44, such as disclosed in U.S. Pat. Nos. 8,709,337 and 8,931,711. A breathable membrane 46 is a vapor permeable membrane that prevents free flow of liquid out of the membrane, thus addressing leakage problems. Suitable membranes include, but are not limited to, UHMWPE-type membrane optionally filled with silica as described in U.S. Pat. No. 7,498,369. Such UHMWPE membranes include Daramic™ V5, available from Daramic, Solupor®, available from DSM (Netherlands), and Teslin™ SP1100HD, available from PPG Industries, and combinations thereof. Other suitable breathable membranes include any permeable polymeric, thermoplastic, or thermoset material, including acetal, acrylic, cellulosic, fluoroplastic, polyamide, polyester, polyvinyl, polyolefin, styrenic, etc, alone, co-extruded, woven or non-woven, mixed or in combination with elastomers, rubber, solids, silicas, or combinations thereof. Also suitable are Hytrel™ available from Dupont or Lotryl™ available from Arkema. The delivery engine 42, such as shown in FIG. 3, may also include a rupturable substrate 48 that seals the freshening composition in the liquid reservoir until a rupture mechanism 50 is engaged to when the apparatus is to be used by the consumer. When the consumer is ready to use the apparatus, the consumer can rupture the rupturable substrate 48 with the rupture mechanism 50, which allows the freshening composition in the liquid reservoir 44 to contact the breathable membrane.

The air care product may not be in the form of an on-demand or spray product such as an aerosol or mechanical spray product as the benefits of isopropyl myristate in the freshening composition will not be realized in an on-demand type product.

EXAMPLES

Method:

The data contained herein consists of evaporative weight-loss, or stated another way, the cumulative daily loss of weight from a delivery engine as expressed in terms of mg/day ("weight-loss"). To determine the weight-loss through evaporation the freshening composition which is evaporating is weighed on a regular basis and at any point in time, the total mg/day evaporated is calculated by comparing the weights from two adjacent time points as well as the time that has elapsed between the aforementioned points at which the weight was recorded:

$$g/Hr = \frac{[(\text{Weight in mg at time point 1}) - (\text{Weight in mg at time point 2})]}{\text{Elapsed time (in Hours)}}$$

$g/Hr = (g/Hr) * (1000 \text{ mg}/1 \text{ g}) = \text{mg/Hour}.$ $\text{mg/Day} = (\text{mg}/Hr) * \#$ of Days elapsed in terms of hours Cumulative mg = Summation of mg/Day across the given number of days Cumulative Weight loss at Day "X" == Day $1_{(mg/Day)}$ + Day$2_{(mg/Day)}$ + ... Day $X_{(mg/Day)}$ Sample Calculations:

Test Sample 1, on Day 1, weighs 100.00 g at 3:00 p.m.
Test Sample 1, on Day 2, weighs 99.50 g at 3:00 p.m. (24 hours of elapsed time)
Test Sample 1, on Day 3, weighs 99.05 g at 3:00 p.m. (24 hours of elapsed time)
Test Sample 1, on Day 4, weighs 98.63 g at 3:00 p.m. (24 hours of elapsed time)
The evaporation rate in mg/hr=
  Day 1 to Day 2:
    g/Hr Rate=(100.00 g−99.50 g)/24 hours=0.02083 g/Hr
    mg/Hr Rate=0.0208 g/Hr*1000 mg/1 g=20.83 mg/Hr.
  Day 2 to Day 3:
    g/Hr Rate=(99.50 g−99.05 g)/24 hours=0.01875 g/Hr
    mg/Hr Rate=0.01875 g/Hr*1000 mg/1 g=18.75 mg/Hr.
  Day 3 to Day 4:
    g/Hr Rate=(99.05 g−98.63 g)/24 hours=0.0175 g/Hr
    mg/Hr Rate=0.0175 g/Hr*1000 mg/1 g=17.5 mg/Hr.
The evaporation rate in mg/Day=
  Day 1 to Day 2:
    mg/Day=(20.83 mg/Hr)*(24 hour/1 Day)=499.92 mg/Day
  Day 2 to Day 3:
    mg/Day=(18.75 mg/Hr)*(24 hour/1 Day)=450.00 mg/Day
  Day 3 to Day 4:
    mg/Day=(17.5 mg/Hr)*(24 hour/1 Day)=420.00 mg/Day The cumulative weight loss through Day 3 is 1369.92 mg, as illustrated in the TABLE 2 below.

TABLE 2

| Time (Days): | Cumulative Evaporation (mg): |
| --- | --- |
| Day 1 | 499.92 mg |
| Day 2 | 949.92 mg = (499.92 mg Day 1) + (450 mg Day 2) |
| Day 3 | 1369.92 mg = (499.92 mg Day 1) + (450 mg Day 2) + (420 mg Day 3). |

Enabling Extended Longevity in Low Concentrated Perfume Formulations (<65% Perfume Oil):

Example A

The freshening compositions of Example A were evaporated from an AMBI PUR™ diffuser having a single wick (~12.00 mm exposed wick length, ~6.5 mm diameter) while plugged in for 24 hours per day. The freshening compositions were evaporated until at least 85% of the liquid freshening composition had been exhausted from the reservoir. For Example A, the only variable in the freshening compositions is the change in concentration of IPM. The freshening compositions tested in Example A are shown below in TABLE 3. The "+1.5% IPM" freshening composition has a vapor pressure at 25° C. of about 0.26 Torr. The evaporative weight-loss results of Example A are shown in FIG. 4.

TABLE 3

| Freshening Composition Name | % Non-Functional Perfume Component: | % Tripropylene Glycol Methyl Ether ("TPM") | % Isopropyl Myristate ("IPM") |
| --- | --- | --- | --- |
| 0% IPM | 59% | 41% | 0% |
| +1.5% IPM | 59% | 39.5% | 1.5% |
| +2.0% IPM | 59% | 39% | 2% |

As shown in FIG. 4, the addition of IPM at 1.5 wt. % and 2.0 wt. % significantly increased the elapsed evaporation time of the freshening compositions of Example A.

Example B

The freshening compositions of Example B were individually evaporated from an AMBI PUR™ diffuser having a single heated wick (~12.00 mm exposed wick length, ~6.5 mm diameter) while plugged in for 24 hours per day. The freshening compositions were evaporated until at least 85% of the liquid freshening compositions had been exhausted from the reservoir. For Example B, the only variable in the freshening compositions is the change in concentration of IPM. The freshening compositions tested in Example B are shown below in TABLE 4. The "+1.0% IPM" freshening composition has a vapor pressure at 25° C. of about 0.1 Torr. The evaporative weight-loss results of Example B are shown in FIG. 5.

TABLE 4

| Freshening Composition Name | % Non-Functional Perfume Component: | % Tripropylene Glycol Methyl Ether ("TPM") | % Isopropyl Myristate ("IPM") |
|---|---|---|---|
| 0% IPM | 63.5% | 36.5% | 0% |
| +1.0% IPM | 63.5% | 35.5% | 1% |
| +1.5% IPM | 63.5% | 35% | 1.5% |

As shown in FIG. 5, the addition of IPM at 1.0 wt. % and 1.5 wt. % significantly increased the elapsed evaporation time of the freshening compositions of Example B.

Example C

The freshening compositions of Example C were individually evaporated from an AMBI PUR™ diffuser having a single heated wick (~12.00 mm exposed wick length, ~6.5 mm diameter) while plugged in for 24 hours per day. The freshening compositions were evaporated until at least 85% of the liquid freshening compositions had been exhausted from the reservoir. For Example C, the only variable in the freshening compositions is the change in concentration of IPM. The freshening compositions tested in Example C are shown below in TABLE 5. The "2.5% IPM" freshening composition has a vapor pressure at 25° C. of about 0.16 Torr. The evaporative weight-loss results of Example C are shown in FIG. 6.

TABLE 5

| Freshening Composition | Non-Functional Perfume Component | % Tripropylene Glycol Methyl Ether ("TPM") | % Dipropylene Glycol Methyl Ether ("DPM") | % Isopropyl Myristate ("IPM") |
|---|---|---|---|---|
| 0% IPM | 30% | 49% | 21% | 0% |
| 2.5% IPM | 30% | 49% | 18.5% | 2.5% |
| 11.6% IPM | 30% | 49% | 9.4% | 11.6% |
| 23% IPM | 30% | 47% | 0% | 23% |

As shown in FIG. 6, the addition of 2.5 wt. % IPM and 11.6 wt. % IPM increased the elapsed evaporation time of the freshening compositions of Example C. With the addition of 23 wt. % IPM, FIG. 6 illustrates that the benefit of IPM levels off, as the results are comparable to the 11.6 wt. % IPM.

Example D

The freshening compositions of Example D were individually evaporated from an AMBI PUR™ diffuser having three heated wicks (~12.00 mm exposed wick length/4.0 mm diameter) while plugged in for 12 hours per day. The freshening compositions were evaporated for sufficient time so as to either attain "end of life," as detailed in the graph below, or until sufficient evaporative data had been collected. For Example D, the only variable in the freshening compositions is the change in concentration of IPM. The freshening compositions tested in Example D are shown below in TABLE 6. The "2.5% IPM" freshening composition has a vapor pressure at 25° C. of about 0.16 Torr. The evaporative weight-loss results of Example D are shown in FIG. 7.

TABLE 6

| Freshening Composition | Non-Functional Perfume Component | % Tripropylene Glycol Methyl Ether ("TPM") | % Dipropylene Glycol Methyl Ether ("DPM") | % Isopropyl Myristate ("IPM") |
|---|---|---|---|---|
| 0% IPM | 30% | 49% | 21% | 0% |
| 2.5% IPM | 30% | 49% | 18.5% | 2.5% |
| 11.6% IPM | 30% | 49% | 9.4% | 11.6% |
| 23% IPM | 30% | 47% | 0% | 23% |

As shown in FIG. 7, the addition of 2.5 wt. % IPM and 11.6 wt. % IPM increased the elapsed evaporation time of the freshening compositions of Example D. With the addition of 23 wt. % IPM, FIG. 7 illustrates that the benefit of IPM levels off, as the results are comparable to the 11.6 wt. % IPM.

Enabling Extended Longevity of Concentrated (>65% Perfume Oil) Formulations:

Example E

The freshening compositions of Example E were individually evaporated from an AMBI PUR™ diffuser having a single wick (~12.00 mm exposed wick length, ~6.5 mm diameter) while plugged in for 24 hours per day. The freshening compositions were evaporated for sufficient time so as to either attain "end of life," as detailed in the graph below, or until sufficient evaporative data had been collected. For Example E, the non-functional perfume raw material portion of the freshening composition accounts for 90% of the total freshening composition. The remaining balance of 10% of the freshening compositions consists only carrier materials, specifically DOWANOL™ TPM and "IPM." The freshening compositions tested in Example E are shown below in TABLE 7. The "+2% IPM" freshening composition has a vapor pressure at 25° C. of about 0.5 Torr. The evaporative weight-loss results of Example E are shown in FIG. 8.

TABLE 7

| Freshening Composition Name | % Non-Functional Perfume Component: | % Tripropylene Glycol Methyl Ether ("TPM") | % Isopropyl Myristate ("IPM") |
|---|---|---|---|
| 0% IPM | 90% | 10% | 0% |
| +2% IPM | 90% | 8% | 2% |
| +4% IPM | 90% | 6% | 4% |
| +6% IPM | 90% | 4% | 6% |
| +8% IPM | 90% | 2% | 8% |

FIG. 8 shows the evaporation profile of the freshening compositions of Example E. The +2% IPM, +4% IPM, +6% IPM, and +8% IPM compositions were evaluated over a 15-day period, while the 0% IPM composition was evaluated over a 20-day period. The elapsed evaporation time would extend significantly past the 15-day period that the compositions were tested. Thus, FIG. 8 illustrates that the addition of low levels of IPM dramatically increases the elapsed evaporation time of the freshening compositions, even at low overall carrier levels and high non-functional perfume raw material levels.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values, any integers within the specified range, and any ranges with the specified range. For example a range disclosed as "1 to 10" is intended to mean "1, 2, 3, 4, 5, 6, 7, 8, 9, 10."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid freshening composition comprising:
   about 0.5 wt. % to about 3.0 wt. % isopropyl myristate, by weight of the liquid freshening composition; and
   greater than 30 wt. % of one or more non-functional perfume raw materials, by weight of the liquid freshening composition,
   wherein the liquid freshening composition has a vapor pressure at 25° C. of about 0.03 Torr to about 1.0 Torr.

2. The liquid freshening composition of claim 1 further comprising less than 50 wt. % of a carrier, by weight of the liquid freshening composition.

3. The liquid freshening composition of claim 1 further comprising less than 30 wt. % of a carrier, by weight of the liquid freshening composition.

4. The liquid freshening composition of claim 1, wherein the liquid freshening composition has a vapor pressure at 25° C. of about 0.03 Torr to about 0.75 Torr.

5. The liquid freshening composition of claim 1 further comprising an active agent.

6. An air freshener product comprising:
   a liquid freshening composition comprising about 0.5 wt. % to about 3.0 wt. % isopropyl myristate and greater than 40 wt. % of one or more perfume raw materials, by weight of the liquid freshening composition, wherein the liquid freshening composition has a vapor pressure at 25° C. of about 0.03 Torr to about 0.75 Torr;
   a reservoir for containing the liquid freshening composition; and
   a delivery engine in fluid communication with the liquid freshening composition,
   wherein the delivery engine is selected from the group consisting of: wick, gel, porous and semi-porous substrate, and combinations thereof.

7. The air freshener product of claim 6, wherein the delivery engine is a wick or a breathable membrane.

8. The air freshener product of claim 6 further comprising an evaporative assistance element is selected from the group consisting of: a heater, a fan, an agitator, and combinations thereof.

9. The air freshener product of claim 8, wherein the evaporative assistance element is a heater, wherein the heater is configured to heat the delivery engine to a temperature in the range of about 50° C. to about 150° C.

10. The air freshener product of claim 6, wherein the liquid freshening composition comprises less than 30 wt. % of a carrier, by weight of the liquid freshening composition.

11. The air freshener product of claim 6, wherein the liquid freshening composition has a vapor pressure at 25° C. of about 0.03 Torr to about 0.75 Torr.

12. A method of freshening the air comprising the steps of:
    providing a freshening composition comprising about 0.5 wt. % to about 3.0 wt. % isopropyl myristate and greater than 40 wt. % of one or more perfume raw materials, by weight of the liquid freshening composition, wherein the liquid freshening composition has a vapor pressure at 25° C. of about 0.03 Torr to about 1.0 Torr;
    delivering the liquid freshening composition to a delivery engine, wherein the delivery engine is selected from the group consisting of: wick, gel, porous and semi-porous substrate, and combinations thereof; and
    dispersing the liquid freshening composition into the air.

13. The method of claim 12 further comprising the step of heating the delivery engine to a temperature in the range of about 50° C. to about 150° C.

14. The method of claim 12 further comprising less than 50 wt. % of a carrier, by weight of the liquid freshening composition.

15. The method of claim 12, wherein the step of dispersing the liquid freshening composition into the air includes evaporating the liquid freshening composition into the air.

16. The method of claim 12 comprising about 0.75 wt. % to about 3.0 wt. % isopropyl myristate, by weight of the liquid freshening composition.

17. The method of claim 12, wherein the liquid freshening composition has a vapor pressure at 25° C. of about 0.03 Torr to about 0.75 Torr.

18. The method of claim 12, wherein the step of dispersing the liquid freshening composition further comprising dispersing the liquid freshening composition using an evaporative assistance element, wherein the evaporative assistance element is selected from the group consisting of: a heater, a fan, an agitator, and combinations thereof.

* * * * *